US012778561B2

(12) United States Patent
Huber et al.

(10) Patent No.: US 12,778,561 B2
(45) Date of Patent: Nov. 3, 2026

(54) ULTRASOUND REMOTE MONITORING, OPERATING AND TRAINING SYSTEM

(71) Applicant: Oncura Partners Diagnostics, LLC, Fort Worth, TX (US)

(72) Inventors: Brian Huber, Rowlett, TX (US); Craig Presnall, Fort Worth, TX (US)

(73) Assignee: Oncura Partners Diagnostics, LLC, Fort Worth, TX (US)

( * ) Notice: Subject to any disclaimer, the term of this patent is extended or adjusted under 35 U.S.C. 154(b) by 0 days.

(21) Appl. No.: 18/808,570

(22) Filed: Aug. 19, 2024

(65) Prior Publication Data

US 2024/0415495 A1 Dec. 19, 2024

Related U.S. Application Data

(63) Continuation of application No. 17/008,307, filed on Aug. 31, 2020, now Pat. No. 12,064,289, and a continuation of application No. 14/823,609, filed on Aug. 11, 2015, now Pat. No. 10,758,210.

(60) Provisional application No. 62/167,458, filed on May 28, 2015, provisional application No. 62/040,642, filed on Aug. 22, 2014.

(51) Int. Cl.
*A61B 8/00* (2006.01)

(52) U.S. Cl.
CPC .............. *A61B 8/56* (2013.01); *A61B 8/4405* (2013.01)

(58) Field of Classification Search
CPC ................................ A61B 8/4405; A61B 8/56
See application file for complete search history.

(56) References Cited

U.S. PATENT DOCUMENTS

| | | | |
|---|---|---|---|
| 5,938,607 | A | 8/1999 | Jago et al. |
| 6,516,318 | B2 | 2/2003 | Nakamura et al. |
| 7,346,174 | B1 | 3/2008 | Smith |
| 8,038,622 | B2 | 10/2011 | Abraham |
| 8,147,414 | B2 | 4/2012 | Abraham |
| 8,235,903 | B2 | 8/2012 | Abraham |
| 8,403,858 | B2 | 3/2013 | Abraham |
| 8,509,513 | B2 | 8/2013 | Prion et al. |
| 8,708,909 | B2 | 4/2014 | Goertz et al. |
| 9,149,257 | B2 | 10/2015 | Abraham |
| 9,855,021 | B2 | 1/2018 | Abraham |
| 2002/0193679 | A1 | 12/2002 | Malave et al. |
| 2004/0015079 | A1 | 1/2004 | Berger et al. |
| 2004/0024306 | A1 | 2/2004 | Hamilton et al. |
| 2004/0030227 | A1 | 2/2004 | Littrup et al. |
| 2006/0116577 | A1 | 6/2006 | Dewitt |

(Continued)

*Primary Examiner* — Alexei Bykhovski
(74) *Attorney, Agent, or Firm* — Fish IP Law, LLP

(57) ABSTRACT

The present invention is a method, system, and apparatus used to transmit information to an individual and or receiver who is not located at the actual ultrasound procedure that may monitor, communicate, and assist in the procedure in real time as well as provide protocols for specific procedures; wherein the ultrasound machine communicates to a receiver operational information such as but not limited to audio, visual, performance, and so forth; wherein the information may be received in real time to another party not located at the site of the procedure who may assist with the procedure, training, protocols, and so forth; and wherein the receiver may then transmit back to the ultrasound machine specific directions as well as communicate with the ultrasound operator.

15 Claims, 2 Drawing Sheets

(56) References Cited

U.S. PATENT DOCUMENTS

| | | | | |
|---|---|---|---|---|
| 2007/0041647 | A1 | 2/2007 | Florin et al. | |
| 2007/0130287 | A1 | 6/2007 | Kumar et al. | |
| 2007/0161898 | A1 | 7/2007 | Hao et al. | |
| 2007/0203748 | A1 | 8/2007 | Rothpearl et al. | |
| 2009/0125147 | A1* | 5/2009 | Wang | G06T 7/0012<br>715/764 |
| 2011/0055148 | A1 | 3/2011 | Berg et al. | |
| 2011/0160582 | A1 | 6/2011 | Zheng et al. | |
| 2011/0213210 | A1 | 9/2011 | Temby et al. | |
| 2012/0184955 | A1 | 7/2012 | Pivotto et al. | |
| 2012/0321168 | A1 | 12/2012 | Deitz | |
| 2013/0197401 | A1 | 8/2013 | Sato et al. | |
| 2013/0345566 | A1 | 12/2013 | Weitzel et al. | |
| 2014/0039277 | A1 | 2/2014 | Abraham | |
| 2014/0050375 | A1 | 2/2014 | Baker et al. | |
| 2014/0142982 | A1 | 5/2014 | Janssens | |
| 2014/0180111 | A1* | 6/2014 | Gopinathan | A61B 8/483<br>600/447 |
| 2014/0236016 | A1 | 8/2014 | Morgan | |
| 2014/0276056 | A1 | 9/2014 | Ohta et al. | |
| 2015/0119652 | A1 | 4/2015 | Hyde et al. | |
| 2015/0223767 | A1 | 8/2015 | Sehnert et al. | |
| 2016/0003926 | A1 | 1/2016 | Boettcher | |
| 2018/0116630 | A1 | 5/2018 | Dykes et al. | |

* cited by examiner

ULTRASOUND REMOTE MONITORING, OPERATING AND TRAINING SYSTEM

CROSS-REFERENCE TO RELATED APPLICATIONS

This application is a continuation of and claims the benefit of priority to U.S. Ser. No. 17/008,307 filed Aug. 31, 2020, which is a continuation of and claims the benefit of priority to U.S. Ser. No. 14/823,609 filed Aug. 11, 2015, which claims priority from provisional patent application U.S. Ser. No. 62/040,642 filed on Aug. 22, 2014 and priority from provisional patent application U.S. Ser. No. 62/167,458 filed on May 28, 2015, each of which is incorporated in its entirety by reference herein.

BACKGROUND OF INVENTION

Field of the Invention

In general, the present invention relates to a device, system and method of remotely monitoring, operating, and training for ultrasound medical devices. More particularly, the present invention provides an ultrasound machine and associated equipment that is capable of transmitting and receiving in real time to a remote location wherein another individual may assist, operate, train and so forth the user of the ultrasound machine. It is also contemplated to provide specific protocols for ultrasound procedures as well as modification of an ultrasound machine.

Description of the Prior Art

Ultrasound is an oscillating sound pressure wave with a frequency greater than the upper limit of the human hearing range. Ultrasound is thus not separated from 'normal' (audible) sound by differences in physical properties, only by the fact that humans cannot hear it. Although this limit varies from person to person, it is approximately 20 kilohertz (20,000 hertz) in healthy, young adults. Ultrasound devices operate with frequencies from 20 kHz up to several gigahertz. Ultrasound is used in many different fields. Ultrasonic devices are used to detect objects and measure distances. Ultrasonic imaging (sonography) is used in both veterinary medicine and human medicine.

Medical sonography (ultrasonography) is an ultrasound-based diagnostic medical imaging technique used to visualize muscles, tendons, and many internal organs, to capture their size, structure and any pathological lesions with real time tomographic images. Ultrasound has been used by radiologists and sonographers to image the human body and animals for at least 50 years and has become a widely used diagnostic tool. The technology is relatively inexpensive and portable, especially when compared with other techniques, such as magnetic resonance imaging (MRI) and computed tomography (CT).

Ultrasound is also used to visualize fetuses during routine and emergency prenatal care. Such diagnostic applications used during pregnancy are referred to as obstetric sonography. As currently applied in the medical field, properly performed ultrasound poses no known risks to the patient. Sonography does not use ionizing radiation, and the power levels used for imaging are too low to cause adverse heating or pressure effects in tissue.

Ultrasound is also increasingly being used in trauma and first aid cases, with emergency ultrasound becoming a staple of most EMT response teams. Furthermore, ultrasound is used in remote diagnosis cases where teleconsultation is required, such as scientific experiments in space or mobile sports team diagnosis.

In fine needle aspiration biopsy (FNAB), the doctor (a pathologist, radiologist, veterinarian, or surgeon) uses a very thin needle attached to a syringe to withdraw (aspirate) a small amount of tissue from the suspicious area. This tissue is then looked at under a microscope. The needle used for FNAB is thinner than the ones used for blood tests. If the area to be biopsied can be felt, the doctor locates the lump or suspicious area and guides the needle there. If the lump cannot be felt, the doctor might use ultrasound to watch the needle on a screen as it moves toward and into the mass. This is called an ultrasound-guided biopsy. Or, the doctor may use a method called stereotactic needle biopsy to guide the needle. For a stereotactic needle biopsy, computers map the exact location of the mass using mammograms taken from two angles. This helps the doctor guide the needle to the right spot.

Ultrasound use in veterinary medicine has been a significant challenge at the general practice levels. The training in veterinary colleges consists of about a three-week course in ultrasound as part of their diagnostic radiology courses. The vast majority of general practitioners and even specialists will need extensive additional post-graduate training to become proficient and confident to use and interpret this modality in their day-to-day medical practices.

Training has always consisted of going off site to a seminar for a few days, or taking courses at veterinary conferences, then going back to their practice and using what knowledge they have just obtained. The problem with this is that it is known, by education standards, that the class attendants only retain about 20-30% at best of what they just learned. Often, the training is on advanced ultrasound equipment unlike what the actual equipment is in the hospital setting.

Traditionally, ultrasound diagnostics will take years to develop the techniques, understanding of the physics of this modality and ultimately the confidence to be able to diagnose abnormalities in the patient. The veterinarian will spend thousands of dollars, easily a $20-30,000 education investment, and years to become confident.

Of all the current ultrasound equipment in the veterinary medical field, less than 10% is actually being fully utilized as it should due to the difficulty of accessing long-term training and support on interpretation of these ultrasound examination procedures. Furthermore, most companies that sell ultrasound machines leave it up to the purchaser to acquire training and knowledge to integrate this diagnostic platform into their practice.

Thus, there is a need for a product that fills the needs of the industry. It is desirable to fill these needs at rates that are affordable and attractive to ultrasound users while also providing a means to train, assist, operate and monitor the procedure. The above discussed limitations in the prior art is not exhaustive. The current invention provides an inexpensive, time saving, more reliable apparatus, system and method where the prior art fails.

SUMMARY OF THE INVENTION

In view of the foregoing disadvantages inherent in the known types of equipment and methods of use now present in the prior art, the present invention provides a new and improved apparatus, system and method of use that provides real time remote operation, training and monitoring of an ultrasound procedure anywhere in the world. As such, the general purpose of the present invention, which will be described subsequently in greater detail, is to provide a new and improved remote monitoring and operating of ultrasound equipment in general, which has all the advantages of the prior art devices and none of the disadvantages.

Therefore, it is contemplated that the present invention is a method, system and apparatus used to transmit information to an individual who is not located at the actual ultrasound procedure that may monitor, communicate and assist in the procedure in real time as well as provide protocols for specific procedures. In a preferred embodiment, an ultrasound machine communicates to a receiver operational information such as but not limited to audio, visual, performance and so forth. The information may be received in real time to another party not located at the site of the procedure who may assist with the procedure, training, protocols and so forth. The receiver may then transmit back to the ultrasound machine specific directions as well as communicate with the ultrasound operator. It is also contemplated to modify existing ultrasound machines in the prior art for providing utility with the current invention.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in this application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide a new and improved remote monitoring and operating system for ultrasound procedures that will be capable of allowing an ultrasound operator to communicate, work and train in real time with a remote ultrasound expert via wire and or wireless less communication from two different geographic locations.

Furthermore, an object of the present invention is to provide a new and improved remote monitoring and operating system for ultrasound procedures, which allows for transmitting information via a wireless network in real time to any place on the globe yet still may be easily and efficiently utilized.

Another object of the present invention is to provide a new and improved remote monitoring, training and operating system for ultrasound procedures that has a very simple user interface and as such requires minimal training and time to operate.

It is a further object of the present invention to provide a new and improved remote monitoring, training and operating system for ultrasound procedures, which is of a durable and reliable construction and may be utilized in any location including offshore applications.

An even further object of the present invention is to provide a new and improved remote monitoring, training and operating system for ultrasound procedures, which is susceptible to a low cost of installation with regard to both hardware, software and labor, which accordingly is then susceptible to low prices of sale to the consuming industry, thereby making such a system economically available to those in the field.

Still another object of the present invention is to provide a new and improved remote monitoring, training and operating system for ultrasound procedures, which provides all of the advantages of the prior art on site monitoring, while simultaneously overcoming some of the disadvantages normally associated therewith.

Another object of the present invention is to provide a new and improved remote monitoring, training and operating system for ultrasound procedures, which may be used for humans, animals, and other industrial procedures.

Yet another object of the present invention is to provide a new and improved remote monitoring, training and operating system for ultrasound procedures, which provides for real time operational feedback and provides the necessary training for same.

An even further object of the present invention is to provide a new and improved remote monitoring, training and operating system for ultrasound procedures that provides specific protocols for procedures that may be utilized by a practitioner who is in need of same.

Still another object of the present invention is to provide a new and improved remote monitoring, training and operating system for ultrasound procedures that may utilize ultrasound equipment in general and may also be utilized with veterinary ultrasound systems sold by Analogic Ultrasound Systems Sonix line that may utilize touch screen interface or a traditional console with options designed for veterinary exams.

A further object of the present invention is to provide a new and improved remote monitoring, training and operating system for ultrasound procedures that provides a practitioner an interface for specific procedure protocols for various animals, organs, humans, human organs and so forth.

It is also an object of the present invention to provide a new and improved remote monitoring and operating system for ultrasound procedures that will be capable of modification of existing equipment, such as but not limited to ANALOGIC ULTRASOUND SYSTEM for use with the current invention.

These, together with other objects of the invention, along with the various features of novelty, which characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there are illustrated preferred embodiments of the invention.

BRIEF DESCRIPTION OF THE PICTORIAL ILLUSTRATIONS, GRAPHS, DRAWINGS, AND APPENDICES

The invention will be better understood and objects other than those set forth above will become apparent when consideration is given to the following detailed description thereof. Such description makes reference to the annexed pictorial illustrations, graphs, drawings and appendices.

DETAILED DESCRIPTION OF INVENTION

Figure 1:
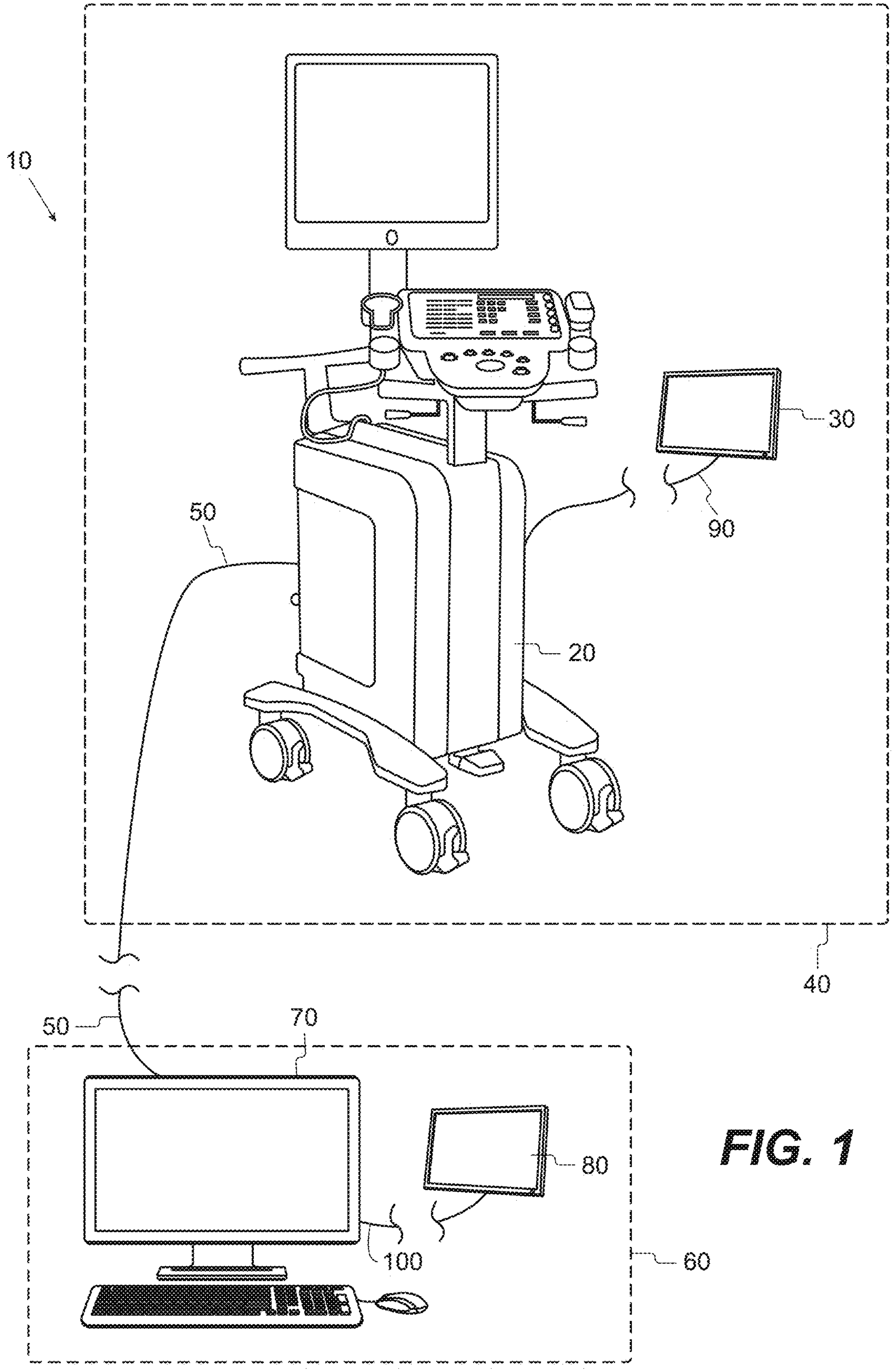
FIG. 1 is a general illustration of a preferred embodiment in accordance with the invention.

Referring to the illustrations, drawings, and pictures and to FIG. 1 in particular, reference character 10 generally designates a new and improved device, system and method of remotely monitoring, operating and training for ultrasound medical devices as well as associated equipment and protocols. For purposes of convenience, the reference numeral 10 may generally be utilized for the indication of the invention, portion of the invention, preferred embodiments of the invention and so on.

Invention 10 contemplates utilization with ultrasound equipment 20 in general and may also be utilized with veterinary ultrasound systems sold by Analogic Ultrasound Systems Sonix line that may utilize touch screen interface or a traditional console with options designed for veterinary exams. It is understood that numerous types of devices are contemplated. It is also understood the current invention may be utilized in veterinary medicine, human medicine and other industrial applications where ultrasound technology and devices may be utilized.

Invention 10 ultrasound equipment 20 may utilize a first cell phone 30 wherein a first geographic location 40 may transmit and receive visual as well as audio information. This transmission and receiving may be by physical internet connection 50. It is understood that invention 10 contemplates ultrasound equipment 20 may provide visual, video, camera, high definition camera, audio, information and so forth to be transmitted and received via the internet in numerous manners wherein ultrasound equipment 20 may include audio and not need first cell phone 30. It is also understood that physical internet connection 50 may be wireless and so forth as described in greater detail below.

A remote second geographic location 60 may include a computer system 70 capable of sending and receiving from ultrasound equipment 20 as well as first cell phone 30. Second location 60 may include a second cell phone 80 for communication to first cell phone 30 and or ultrasound equipment 20 in general.

It is also understood that first cell phone 30 may be in direct contact 90 and or wireless communication with ultrasound equipment 20 and second cell phone 80 may respectively be in direct contact 100 and wireless contact with computer 70. It is understood that numerous configurations are contemplated.

Communications may be in real time between locations 40 and 60 and further contemplate numerous other locations and invention 10 should not be considered limited to just two locations. It is also understood that numerous means are contemplated to provide communications between same.

Ultrasound equipment 20 may utilize high definition camera 110 that may be operated in real time and remotely allowing sonographers to see and discuss the acquisition of ultrasound images during examinations. It is also contemplated that ultrasound equipment 20 may include more than one camera and may utilize a screen camera 120 as known in the prior art and relatively standard on personal computers. Furthermore, computer 70 may include a screen camera 130 as known in the prior art. Still furthermore, first cell phone 30 may utilize a screen camera 140 and second cell phone 80 may utilize a screen camera 150. This may facilitate face to face communications between the two geographic locations.

Cell phones may utilize CHAT window integration into a platform to allow for more seamless discussion in real time. Invention 10 may utilize RDMS trained sonographers for human applications and or trained on veterinary applications.

Invention 10 may be utilized for veterinary specific training protocols and user manuals specific as well as real time remote training programs where it is contemplated education credits may be obtained for same. This may allow the veterinarians or registered veterinary technicians to obtain training and support at their location and on their time.

Invention 10 may utilize a platform that integrates a PACs workflow to create efficient transmission of these images to specialists for interpretation. This may provide the ability for support personnel to manage the equipment, see the patient, discuss with the actual person performing the procedure and then seamlessly transmit to a specialist for interpretation.

Invention 10 contemplates numerous platforms known in the art and that may be utilized in the future for remote education and real time support associated with abdominal, musculoskeletal, ocular, soft tissue and echo cardiology. Further contemplated are all remote education and real time support associated with interventional techniques particularly guided FNA and biopsy techniques, paracentesis procedures as well as abdominocentesis, thoracocentesis, pericardiocentesis, intra-articular injections, and so forth.

Invention 10 may be utilized with support personnel in veterinary medicine such as but not limited to board certified radiologists, cardiologists, internal medicine specialists, ABVP specialists or qualified veterinary practitioners. Furthermore, invention 10 may be utilized by human trained and certified sonographers performing veterinary ultrasound, qualified registered or licensed veterinary technicians. Still further, invention 10 may be utilized by support personnel in human medicine such as but not limited to board certified radiologists, cardiologists and internists, human sonographers (all RDMS certification levels or not), chiropractors, emergency medicine clinicians, licensed nurses and so forth.

It is also contemplated that invention 10 may provide remote real time support such that education moves the doctor and or technician into acquiring ultrasound diagnostic exams in 60-90 days versus five years with normal education. It is also contemplated to provide training and education platforms that provide a certification process that may be after the basic abdominal or echo cardiology training program with the next possibly being a required certification exam. Once passed, the trained sonographer may be allowed to send ultrasound exams into specialists for interpretation.

Therefore invention 10 contemplates remote location and in real time with camera wherein the patient and person handling the ultrasound probe can be seen, communications with the person via phone or speaker system embedded in equipment, using a CHAT feature to start communications or discuss patient needs or activate a session; allowing working directly with the person and or medical professional to train, educate and support ultrasound guided biopsy procedures, remotely and in real time; auto integration of medical workflow processes on DVR's, Cine Loops and static images of Ultrasounds; ability to remotely manage post-process of ultrasound images such as but not limited to pulling up data on exam after a patient has left and improve imaging, labels, etc. prior to submission; remotely measure and create information for specialists to interpret that may be sent thru Telemedicine PACs programs; all aspects of internet, satellite or combination of those technologies that allow this remote real time information to flow; develop the unique remote real time sales process of having the sonographer demonstrate unit during a live sales presentation; animal specific training parameters; online training protocols for all organs; provide a Linear 14-5 mHz transducer to create small animal specific training programs; introduction of using transducer biopsy clips and needle guides in veterinary medicine; introduction of real-time ultrasound guidance positioning system with remote sonographer support; and so forth.

Another Preferred Embodiment

Figure 2:
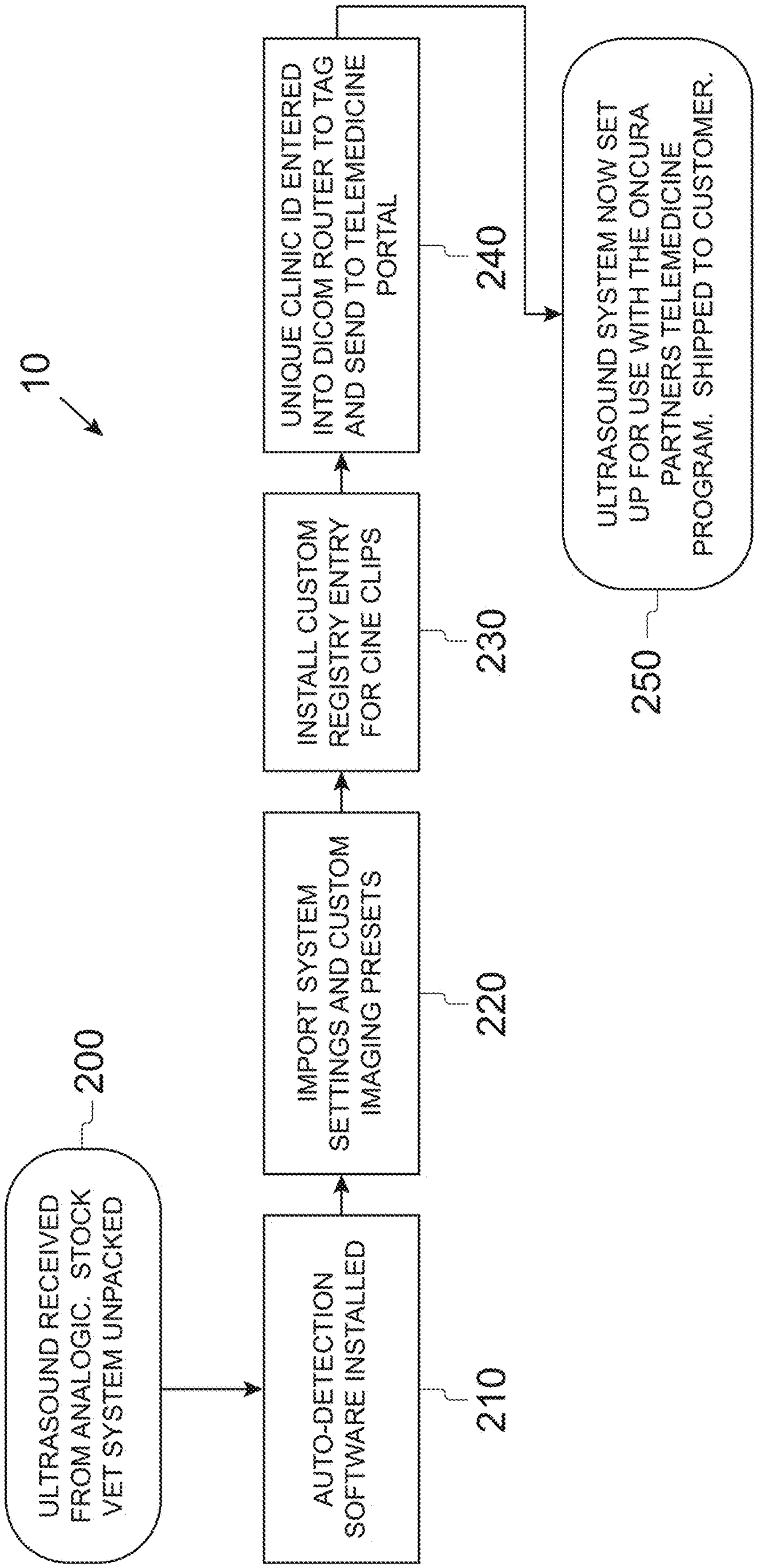
FIG. 2 is a general flowchart illustration of a preferred embodiment in accordance with the invention.

Referring to the illustrations in general and more in particular to FIG. 2, invention 10 further contemplates modification of existing ultrasound equipment such as but not limited to a ANALOGIC ULTRASOUND SYSTEM for use with the current invention. It is contemplated that after an ultrasound is received, stock vet system 200 is unpacked and auto detection software 210 may be installed. This may regulate the disk space because of the heavy usage of raw data for post-processing of images. It is contemplated that after two days, raw data only is removed from the patient files. Demographics, images, clips, reports and so forth may be retained. It is contemplated the hard disk space would be full after 5 to 6 exams otherwise.

Invention 10 contemplates importing system settings and custom imaging presets 220. This may improve imaging presets over the system defaults and or annotations that follow the protocol and system functionality settings that are imported into the ultrasound software. Unique clinic identifiers may be assigned for AE titles, operators, attending fields, and so forth.

It is also contemplated to install custom registry entry for cine clips 230. This registry entry may enable the capture of longer cine clips while minimizing the load on available system memory. It may provide seven seconds and or greater versus the default system maximum of three seconds.

Invention 10 further contemplates unique clinic ID entered into DICOM router to tag and send to telemedicine portal 240. The DICOM router may append the unique clinic ID to each transferred image and clip so that it can be properly archived on the telemedicine platform. It is contemplated that without, exams would go unassigned to clinics. It is understood that invention 10 may provide ultrasound system set up for use with the current invention telemedicine program and shipped to customer 250.

Operating Systems

In a preferred embodiment, the invention may generally utilize a computer system. The system may include various input/output (I/O) devices (e.g., mouse, keyboard, display, Internet-enabled mobile phone, and Internet-enabled PDA) and one or more general purpose computers having a central processor unit (CPU), an I/O unit and a memory that stores data and various programs such as an operating system, and one or more authoring applications (e.g., programs for word processing, creating spread sheets, and producing graphics), one or more client applications (e.g., programs for accessing online services), and one or more browser applications (e.g., programs for retrieving and viewing electronic documents from the Internet and/or Web). The computer system may also include a communications device (e.g., a satellite receiver, a modem, or network adapter) for exchanging data with a host through a communications link (e.g., a telephone line and/or a wireless link) and/or a network.

It is contemplated that the invention may be activated, accessed, utilized and so forth by the use of a computer screen related desktop icon for instantaneous retrieval. It is understood that in a preferred embodiment, the icon will be located in a lower location such as but not limited to a tool bar commonly associated at the bottom right of a computer screen. The invention may be accessed by other means and the icon use should not be considered limiting the scope of the invention. The invention may be utilized with any and all types of internet communication portals. Further, the invention should not be considered limited to existing systems and that the invention may be utilized with other types of internet communication portals.

Likewise, it is contemplated that the invention may be utilized in other means other than a personal computer screen application. It may be utilized with hand held devices, cellular phones, PDAs, and car computer systems or displays. It also includes devices that are mobile, devices that are stationary and or devices that are a combination of mobile and or stationary. It is further contemplated that the invention may be utilized with public phones that may include a visual screen or display to replace or enhance existing phone booths. Likewise, free standing kiosks, booths or other locations may be specifically established to provide a display and access to the invention and said invention may include such established physical access ports, places, kiosks, and the like.

It is still contemplated that the invention may include, utilize, be selectively accessed by specified groups or sub groups, such as a designated entity like a team, community, hospital, agency and so forth. It is contemplated that the invention may include specific promotional materials that companies have produced and would pay the manufacturer or business to appear online with the business that is listed or has an ad or website. This would include any and all types of information including local, regional, national, international and worldwide. It can be placed permanently or temporarily including websites, ads, commercials and any and all types of promotions, advertising, informational and communication data and not excluding any other form or type of knowledge.

It is contemplated that the invention will utilize a computer database accessible through a web-based program or network. The system may have registered members or subscribers who may opt in or pay to be included in the system and who may have access to other information from other members, subscribers, patients and so forth. It is still contemplated, that a preferred construction will be a web-based application with issued access to members and other selected members, databases and so forth. Members may pay per use, time frame orientation, or number of uses or access. In another preferred embodiment, the invention may be carried out as an independent operating system, non-independent operating system, or with features of both.

It is also contemplated that a user may pay for and or receive upgrading that may enable an increased number of individuals to work under a membership, gain access for administrative staff and support-team members, and may remove advertising on pages viewed by upgraded users. It is still also contemplated that a method or system may be utilized to create a means or community through the internet that processes, registers, transfers, and discusses the aforementioned. Members of such may need to complete a login registration and personal validation questionnaire and may need a service provider background check before allowing access. It is understood that numerous ways may be utilized to do the aforementioned as known.

It is contemplated that invention 10 may be able to communicate wirelessly from any location in the world to any other location. It is understood that numerous operations are relatively remote from other types of wireless communications, such as cellular, wherein satellite may be the only option. The invention contemplates providing a signal strength display, warning, alert, and so forth such that the operator knows if a possible communications problem has occurred during communications.

It is therefore contemplated to provide an ultrasound real time remote monitoring, operating and training system comprising an ultrasound machine in a first geographic location adapted to record and transmit an ultrasonic image and further including a camera adapted to record and transmit a visual image of an acquisition of said ultrasound image; a first smartphone in said first geographic location; a computer in a second geographic location in communication such as but not limited the internet, said ultrasound machine and adapted to receive and display said ultrasonic image and said acquisition of said ultrasound image from said camera; and a second smartphone in said second geographic location for communicating with said first smartphone.

It is also therefore contemplated to provide a method of altering an ultrasound machine for use with a monitoring, operating and training system comprising the steps of providing an ultrasound device; installing auto-detection software; importing system settings and custom imaging presets; installing custom registry entry for CINE clips; and entering unique clinic identification into DICOM router to tag and send to telemedicine portal.

Changes may be made in the combinations, operations and arrangements of the various parts and elements described herein without departing from the spirit and scope of the invention. Furthermore, names, titles, headings and general division of the aforementioned are provided for convenience and should, therefore, not be considered limiting.

What is claimed is:

1. An ultrasound real time remote monitoring, operating, and training system comprising:

an ultrasound device in a first geographic location adapted to record and transmit an ultrasonic image and further including a camera adapted to record and transmit a visual image of an acquisition of the ultrasound image;

a first smart device in the first geographic location;

a computer in a second geographic location in communication with the ultrasound device and adapted to receive and display the ultrasonic image and the acquisition of the ultrasound image from the camera; and a second smart device at the second geographic location for communication with the first smart device;

wherein one of the first smart device, second smart device, or the computer enables alteration of duration of a CINE clip captured by the ultrasound device.

2. The ultrasound real time remote monitoring, operating, and training system of claim 1 wherein the computer enables alteration of duration of the CINE clip captured by the ultrasound device from a default duration to another duration.

3. A method of altering an ultrasound device for use with a monitoring, operating and training system comprising the steps:

informationally coupling a computing device to an ultrasound device, wherein the computing device is further informationally coupled to a broadcast device and a remote computing device accessible to a remote user;

providing the ultrasound device access to a software, wherein the software enables importing system settings and custom imaging presets to the ultrasound device; and enabling, by the software, modification of default settings for a CINE clip captured by the ultrasound device.

4. A system comprising:

an ultrasound device at a first location, configured to be operated by a first user;

a broadcast device directed at a portion of the ultrasound machine; and a monitoring station informationally coupled to the broadcast device and the ultrasound machine and configured for operation by a second user at a second location, the monitoring station comprising a visual display and an audio transmitter, wherein the visual display is configured to display a visual signal from each of the broadcast device and the ultrasound machine, and the audio transmitter is configured to transmit an audio signal from the monitoring station to the broadcast device;

wherein the monitoring station provides for modification of a cine clip duration of the ultrasound machine from a default value for the cine clip duration.

5. The system of claim 4, wherein the broadcast device transmits the visual signal to the monitoring station in real time, and wherein the visual signal comprises an image of the portion of the ultrasound machine and an image generated by the ultrasound machine.

6. The system of claim 4, wherein the monitoring station transmits the audio signal and a text via a chat window to the broadcast device in real time, and wherein both the first user and the second user operate the ultrasound machine.

7. The system of claim 4, wherein the monitoring station enables capture of the cine clip by the ultrasound machine, wherein the cine clip is of greater duration than the default value for cine clip duration of the ultrasound machine.

8. The system of claim 4, further comprising an identification tag associated with the visual signal.

9. The system of claim 4, further comprising a router informationally coupled with the broadcast device, wherein the router associates an identification tag with the visual signal.

10. The system of claim 6, wherein the chat window transmits written instructions from the monitoring station to the broadcast device.

11. The system of claim 4, wherein the broadcast device is physically separated from the ultrasound machine.

12. The system of claim 4, wherein raw data from an ultrasound procedure conducted by the ultrasound machine is transferred from the ultrasound machine to the monitoring station.

13. The system of claim 4, wherein the monitoring station transmits both a command to the ultrasound machine and an instruction to the first user.

14. The system of claim 4, wherein the monitoring station is configured to import a procedure specific setting to the ultrasound machine.

15. The system of claim 4, wherein the monitoring station is configured to import an ultrasound image preset specific to a procedure.

* * * * *